United States Patent [19]

Heindel et al.

[11] Patent Number: 5,082,964
[45] Date of Patent: Jan. 21, 1992

[54] SELECTIVE ACETYLCHOLINESTERASE INHIBITORS AND METHODS OF MAKING AND USING SAME

[75] Inventors: Ned D. Heindel, Easton, Pa.; Miguel Turizo, Medellin, Colombia; Hugh D. Burns, Bel Air; Venkataraman Balasubramanian, Baltimore, both of Md.

[73] Assignee: Lehigh University, Bethlehem, Pa.

[21] Appl. No.: 872,677

[22] Filed: Jun. 10, 1986

Related U.S. Application Data

[63] Continuation-in-part of Ser. No. 575,759, Feb. 1, 1984, abandoned.

[51] Int. Cl.$^5$ .............................................. C07C 69/96
[52] U.S. Cl. ...................................... 558/270; 558/273
[58] Field of Search ................................ 558/270, 273

[56] References Cited

U.S. PATENT DOCUMENTS

| | | | |
|---|---|---|---|
| 3,134,802 | 5/1964 | Gaertner et al. | 558/270 |
| 3,420,868 | 1/1969 | Weil | 558/270 X |
| 3,598,856 | 8/1971 | Fujino et al. | 558/270 |
| 4,260,529 | 4/1981 | Letton | 252/547 |

FOREIGN PATENT DOCUMENTS

| | | | |
|---|---|---|---|
| 517285 | 1/1931 | Fed. Rep. of Germany | 558/273 |
| 328082 | 3/1972 | U.S.S.R. | 558/270 |

Primary Examiner—Jose G. Dees
Attorney, Agent, or Firm—Ratner & Prestia

[57] ABSTRACT

A new group of alpha substituted cresol choline carbonate salts, that act as site-specific, irreversible inhibitors of acetylcholinesterase. A halomethylation method and a halogenation method for producing said alpha substituted cresol choline carbonate salts and analogs thereof. Methods of using the inhibitors as anticholinergic insecticides and to reduce acetylcholinesterase activity levels in organisms with excessive levels of acetylcholinesterase.

20 Claims, No Drawings

SELECTIVE ACETYLCHOLINESTERASE INHIBITORS AND METHODS OF MAKING AND USING SAME

This is a continuation-in-part of patent application Ser. No. 575,759, filed Feb. 1, 1984, now abandoned.

BACKGROUND OF THE INVENTION

This invention relates to a new group of specific, irreversible inhibitors of acetyl-cholinesterase (International Enzyme classification EC3.1.1.7) and to methods of making and using these inhibitors.

Acetylcholinesterase is a key enzyme that catalyzes the hydrolysis of acetylcholine to choline and acetic acid via an acyl enzyme intermediate. Along with choline acetyl transferase, acetylcholinesterase regulates the synthesis and metabolism of acetylcholine. Acetylcholinesterase is essential for ganglionic and interneuronal transmission in several parts of the central nervous system.

A number of common abnormalities and physical conditions are characterized by a dysfunction of the production and/or metabolism mechanisms of acetylcholine. Myasthenia gravis, neurological disorders, horse colic, ophthalmological disorders, miotic induction and drug induced extra-pyramidal symptoms which accompany psychiatric drug therapy respond to therapeutic intervention of the cholinergic system. Acetylcholinesterase inhibitors also find uses in the agricultural market as pesticides.

The dysfunction in the production or metabolism mechanisms of acetylcholinesterase can result in excess or deficient levels of this key enzyme substrate in the organism. Inhibitors of acetylcholinesterase may be useful in the treatment and diagnosis of acetylcholinesterase abnormalities, limited by the side effects associated with the administration of the inhibitor under study.

A number of irreversible enzyme inhibitors are known. However, few of them have gained clinical significance, in large part, because of their low specificity for a particular enzyme and their high toxicity.

Known irreversible acetylcholinesterase inhibitors include organophosphorous compounds (see, W. N. Aldridge & E. Reiner, *Enzyme Inhibitors as Substrates. Interaction of Esterases with Esters of Organophosphorous and Carbamic Acids* pp. 1-328 (North Holland, Amsterdam)(1972)), organocarbamates, (see, Aldridge & Reiner, *supra*), sulfonates (see, D. K. Myers & A. Kemp *Nature*, 173, pp. 33-34 (1954)), and arsonates (see, R. Kitz & I. B. Wilson, *J. Biol. Chem.* 237, pp. 3245-49 (1962)). While these irreversible inhibitors bind to the active site of acetylcholinesterase, they also tend to phosphorylate, carbamylate, sulfonate or arsonate any other proteases or esterases which can form an acyl enzyme complex. It is this inactivation of these other enzymes which produces many of the undesirable side effects associated with the use of these inhibitors. In addition, this non-specific binding on other proteases and esterases consumes the inhibitor, thus necessitating larger and more frequent doses of the inhibitor, accompanied again by the undesirable side effects of such treatment.

Other inhibitors of acetylcholinesterase include Methacholine Chloride, Methacholine Bromide, Carbachol, and Bethanechol Chloride (see, *Textbook of Organic Medicinal and Pharmaceutical Chemistry*, (C. Wilson, O. Griswold & R. Doerge eds.) (J. B. Lippincott Co. Philadelphia) pp. 507-10 (1971)). These inhibitors have gained some clinical significance, however the side effects associated with their administration still present clinical problems.

Acetylcholinesterase can be inhibited irreversibly by a group of phosphate esters that are highly toxic. While these inhibitors have marginal clinical usage, until now limited to human clinical experiments for *myasthenis gravia*, they have been used extensively as insecticides. Two examples of such esters include hexaethyltetraphosphate and tetraethyl pyrophosphate. (see, *Textbook of Organic Medicinal and Pharmaceutical Chemistry* pp. 507-10, supra). A problem with these existing acetylcholinesterase inhibitors that are used as insecticides is their general insolubility in petroleum ethers and kerosene. Although somewhat soluble in water, they are quickly deactivated by hydrolysis. This insolubility in the normal spraying oils and instability in water makes application of these insecticides more difficult. (Id. at 510).

Halomethylated derivatives of dihydrocoumarins react biologically on alpha-chymotrypsin in much the same way that the alpha substituted cresol choline carbonates, provided by this invention, react biologically with acetylcholinesterase. The two inhibitors, however, show few structural similarities. (see, Bechet, DuPaix & Blagoeva, Inactivation of alpha-chymotrypsin by new bifunctional reagents: halomethylated derivatives of dihydrocoumarins, Biochemie, 59, 231 (1977)).

Notwithstanding the foregoing, the art has not heretofore taught or suggested an acetylcholinesterase inhibitor that was more specific and of lower systemic toxicity than existing inhibitors; nor has the art suggested an inhibitor of the structural class of this invention.

SUMMARY OF THE INVENTION

The general object of this invention is to provide a site specific, irreversible inhibitor of acetylcholinesterase and methods of producing and using such inhibitors.

More specifically, this invention provides a new group of alpha substituted cresol choline carbonates. In addition, this invention provides a halomethylation method and a halogenation method for producing the alpha-substituted cresol choline carbonates. This invention also provides methods of using the alpha substituted cresol choline carbonates to reduce levels of the active enzyme, acetylcholinesterase, in organisms with more specificity and less systemic toxicity than has heretofore been available.

The compounds of the instant invention are similar in structure with respect to choline. However, precise structural similarity is unnecessary for biological activity so long as a structural/spatial similarity is preserved. For example, as compared to choline, one or more members of the group of the quaternary nitrogen attachments represented as $+N(R_3, R_4, R_5)$ in the general structure of choline may be replaced by a hydrogen or an alkyl group of up to 5 carbon atoms. Furthermore, the general structure of the compound taught by this invention is contemplated to encompass compounds in which quaternary carbon is substituted for the quaternary nitrogen of choline, viz

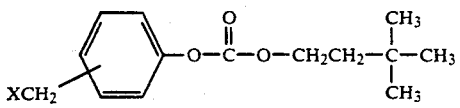

In fact, where the quaternary nitrogen is replaced with quaternary carbon, the compounds retain significant biological activity. These compounds are more lipid soluble and thus can penetrate the biological cell membranes with greater facility.

DETAILED DESCRIPTION OF THE INVENTION

This invention pertains to site specific, irreversible inhibitors of acetylcholinesterase and to methods of producing and using said inhibitors.

This invention identifies a group of new compounds, which can generally be described as alpha substituted cresol choline carbonates of which the molecular structure is:

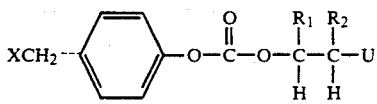

where X= halide or secondary or tertiary amine; U is

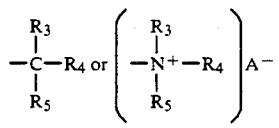

and $A^1$ an anion, either organic or inorganic suitable for forming the salt such as iodide, bromide, chloride, acetate, alkyl sulfate and the like; $R_1$, $R_2$, $R_3$, $R_4$ and $R_5$ = any one or more members of the group consisting of hydrogen and $C_1$ through $C_5$ alkyl groups. A preferred compound is:

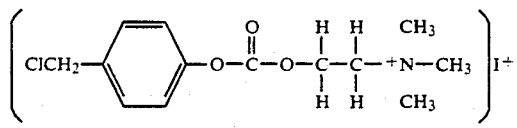

Another preferred compound taught by the instant invention is:

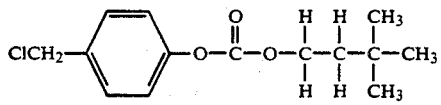

The methods of producing these alpha substituted cresol choline carbonate analogs will be described in detail below with reference to p-chloromethylphenyl-choline carbonate. However, it is to be emphasized that the methods of producing these alpha substituted cresol choline carbonates are not limited to p-chloromethyl-phenylcholine carbonate production.

A halomethylation method of producing an alpha substituted cresol choline carbonate can generally be described as follows. First, an aryl alcohol (phenol) is reacted with phosgene to form an aryl chloroformate; second, the aryl chloroformate is reacted with chloromethyl methyl ether to form p-chloromethyl aryl chloroformate; in the third step, p-chloromethyl aryl chloroformate is reacted with N, N-dimethylethanolamine, and subsequently with an alkylating agent, to form p-chloromethyl aryl choline carbonate in the salt form, with the anion A being as described before.

More specifically, in step one the aryl chloroformates are prepared by condensation of phenol and liquified phosgene in the presence of a basic hydrohalide acceptor. This procedure has previously been described in detail. (see, R. E. Oesper, W. Broker & W. A. Cook, J. Amer. Chem. Soc., 47, 2609 (1925); M. J. Zabik & R. D. Schuetz, J. Org. Chem. 32, 300 (1967); M. Matzner, R. P. Kurkjy & R. J. Cotter, Chem. Reviews 64, 650 (1964)).

In a specific example of the synthesis process of the present invention, 50 mmoles of aryl chloroformate, produced as just described and 50 mmoles of chloromethyl methyl ether were dissolved in 20 ml. of carbon tetrachloride and cooled to $-10°$ C. A solution of antimony pentachloride (25 mmoles) in 5 ml. of carbon tetrachloride was added dropwise with vigorous stirring. The reaction mixture was stirred for five minutes and then poured onto 80 ml. of ice water. The organic layer was separated, dried over magnesium sulfate and evaporated in vacuo. The reaction product, p-chloromethyl phenyl chloroformate, was a viscous liquid which was purified by vacuum distillation.

This chloromethylation procedure is only satisfactory for preparation of para substituted aryl chloroformates, when the precursors possess an unsubstituted para position, or for ortho substituted aryl chloroformates, when the precursors possess a blocked para position and an unsubstituted ortho position.

For all other chloromethyl derivatives in which the $CH_2X$ functionality is desired to be either in the meta- or ortho- position (and the para position is desired to be unsubstituted) the free-radical chlorination as described in Pat. No. 3,420,868 is preferred [Edward D. Weil, assignor to Hooker Chemical Co., filed August 29, 1963]. No matter how the chloromethylphenyl chloroformate is obtained, the subsequent steps are identical.

In the third step of the procedure, as exemplified above, distilled anhydrous N, N-dimethylethanolamine (5.0 ml. 50 moles) was dissolved in ice cold benzene (20 ml.). The ice cold solution of chloromethylphenyl chloroformate (5.38 g., 26 mmoles) in anhydrous benzene (10 ml.) was added dropwise with stirring. The solid which separated was filtered immediately and the filtrate was treated with an excess of methyl iodide (2 ml., 0.032 moles).

After thirty minutes at room temperature, the white precipitate is filtered under a nitrogen atmosphere. The solid is then washed extensively with dry ether. The solid p-chloromethyl phenyl choline carbonate iodide salt which was initially white, was very hygroscopic and turned yellowish on drying.

In the foregoing example, the isolated yields were approximately 75–85% in step one, 30–40% in step two and 80–90% in step three. The final product, p-chloromethyl phenyl choline carbonate iodide salt, can be identified by intense infrared absorption at $1760\pm5$ $cm^{-1}$ and by proton NMR bands at $3.18\pm0.02$ ppm (for the quaternary methyl groups) and $4.78\pm0.02$ ppm (for the halo methylene groups). The substance has a decomposition point of 130° to 133° C., is hygroscopic and crystallizes with a water of hydration. The compound $C_{13}H_{19}ClINO_3 \cdot H_2O$ is calculated to have: $C=37.38$; $H=5.06$ and $N=3.35$, and upon analysis is found: $C=37.70$; $H=4.95$ and $N=3.70$.

In contrast to the halo methylation method previously described and exemplified, the present invention also includes a halogenation method of producing an alpha substituted cresol choline carbonate. This method is generally described as follows. First, a methyl aryl alcohol (cresol) is reacted with phosgene to form methyl aryl chloroformate; second, the methyl aryl chloroformate is reacted with sulfuryl chloride to form p-chloromethyl aryl chloroformate; third, the p-chloromethyl aryl chloroformate is reacted with N, N-dimethylethanolamine, and subsequently with an alkylating agent, to form p-chloromethyl aryl choline carbonate as an ionic salt.

More specifically, in step one the aryl chloroformates are prepared by condensation of cresol and liquified phosgene in the presence of a basic hydrohalide acceptor. The procedure has previously been described in detail. (see, R. E. Oesper, W. Broker & W. A. Cook, J. Amer. Chem. Soc., 47, 2609 (1925); M. J. Zabik & R. D. Schuetz, J. Org. Chem. 32, 300 (1967); M. Matzner, R. P. Kurkjy & R. J. Cotter, Chem. Reviews 64, 50 (1964)).

In step two, the free radical introduction of a chlorine atom onto the cresol chloroformate's methyl group is brought about by ultra-violet photolysis in the presence of sulfuryl chloride. This free radical chlorination procedure is described in Pat. No. 3,420,868 (examples 1 and 2). Yields of 65-75% can be obtained by modification of the patented procedure by excluding the phosphorous trichloride.

Step three is identical to the step three described above in the halomethylation method.

With reference to the molecular structure set forth above, the halo-alkyl ($-CH_2X$) group can be modified by use of a halogen other than chlorine or by replacement with a secondary or tertiary amine (for example, $X=NR_3^+$) An example would be the use of an anhydrous saturated solution of sodium bromide in acetone, which would place a bromine atom on the halomethyl site and exchange the bromine for the iodide atom as the counter-anion in the molecule.

The counteranion (A) can be selected by choice of the alkylating agent employed in step three of either procedure. In addition, the counteranion (A) could be altered by ion-exchange techniques. As previously indicated, the anion may be organic or inorganic. Typical examples are iodide, bromide, chloride, acetate and alkylsulfate and the like.

The synthetic preparation of the hydrochloride salt of the tertiary amine inhibitors involves only slight modifications of the general method. For example, if in the general synthetic method (third step), the solid which separates is filtered immediately and discarded and the filtrate is subjected to the brief passage of a stream of anhydrous HCl gas and then evaporated in brief vacuo, the hydrochloride salt of the N, N-dimethylethyl phenyl carbonate is obtained as a fine, white, water-soluble powder. This substance was tested for its inactivation ability against acetyl-cholinesterase and it showed a time course inactivation similar to that for the p-chloromethylphenyl choline carbonate. From this data it can be deduced that this compound is as potent as the quaternary compound. In fact it showed 88% inactivation in the first 15 minutes at 40 uM concentration.

For the synthetic preparation of the quaternary carbon analogs, 3,3-dimethyl-1-butanol is substituted for N, N-dimethylethanol amine in the general preparation and N, N-dimethylaniline is employed as an acid-acceptor to accelerate the reaction. Thus, a representative procedure is that ca. 25 mmoles of the X-methylene substituted aryl chloroformate (prepared by either of the methods described herein) is dissolved in 20-50 ml of anhydrous benzene and added dropwise to equimolar quantities of 3,3-dimethyl-1-butanol and N, N-dimethylaniline predissolved in 20-50 ml of anhydrous benzene. The mixture was agitated with magnetic stirring for 2 to 8 hours at room temperature, chilled with cold water, and decanted from the precipitate which had formed into a separatory funnel. The organic phase was washed twice with 15 ml portions of water, once with a 15 ml portion of saturated sodium chloride solution, dried over magnesium sulfate, the solvents removed by evaporation in vacuo, and the waxy-oil which separated chilled until crystalline product (50-75%) precipitated. Most 3, 3-dimethylbutyl carbonates prepared by this method were viscous oils or low melting solids (e.g., 3,3-dimethylbutyl phenyl carbonate had a B. P. of 86°-90° C. at 0.25 mm Hg and 3, 3-dimethylbutyl p-chloromethylphenyl carbonate had a melting point of 25-27° C.). The latter compound, displayed an $IC_{50}=8$ $\mu M$ in the Ellman assay.

Ortho-, meta-, and p-chloromethylphenyl choline carbonates are all examples of inhibitors of acetylcholinesterase in accordance with the present invention. Employing the Ellman assay for acetylcholinesterase inhibition [G. L. Ellman, K. D. Courtney, V. Andrews, Jr., and R. M. Featherstone, Biochem. Pharmacol., vol. 7, 88-95 (1961)], the p-chloromethyl derivative, at 25° C. in pH=8, 0.1 molar phosphate buffer, exhibited a $K_i=32$ $\mu M$ and a $K_m$ substrate$=144$ $\mu M$. This specific inhibitor inactives acetylcholinesterase in a time-dependent manner with pseudo first order kinetics below inhibitor concentrations of 40 $\mu M$. Co-inhibition of the enzyme with equimolar concentrations of the substrate acetylcholine and the inhibitor of this invention (10 uM each) during the pre-incubation state offers protection against inactivation. This is believed to show that the inactivation is active site-directed, since the substrate binds to the active site on the enzyme (acetylcholinesterase) leaving no site available for inhibitor binding.

From such competitive inhibitor measurements it was possible to determine an IC50 (proportionate amount necessary to reduce acetylcholinesterase activity by 50%) for various inhibitors [meaning those containing the $CH_2X$ group] in this patent. All $IC_{50}$ values fell between 8 and 200 uM. Representative values obtained are shown below. The exact value varied with the source of the acetylcholinesterase and quantitative measurements were performed on electric eel and human erythrocyte enzyme. Values reported below are with eel-derived enzyme.

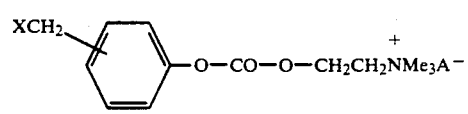

where
$XCH_2 = IC_{50}$
ortho-$CH_2Cl$, $A = 1-100$ $\mu M$ meta-CH$_2$Cl, A = I$^-$ 150 μM
para-CH$_2$Cl, A = I$^-$ 40 μM The inhibitors of acetylcholinesterase described above which are salts are therefore water soluble. Many existing inhibitors are only slightly soluble or insoluble in water. This solubility in water offers advantages when mixing and applying acetylcholinesterase inhibitors as insecticides. In such applications, the inhibitor compounds of this invention would be dissolved in water in an effective insecticidal proportion, as may be easily determined by those skilled in the art, and then sprayed or otherwise dispensed in a conventional manner. Because of their water solubility, the compounds of this invention also offer clinical advantages in the administration of inhibitors to reduce acetylcholinesterase levels in organisms.

p-Chloromethylphenyl choline carbonate iodide salt is an example of an inhibitor of acetylcholinesterase in accordance with the present invention. This compound at 25° C. in pH=8 phosphate buffer exhibits a $K_i$=32 μM and $K_m$ substrate = 144 μM. This specific inhibitor inactivates acetylcholinesterase in a time-dependent manner with pseudo first order kinetics below inhibitor concentrations of 40 μM. Co-incubation of the enzyme with equimolar concentrations of the substrate acetylcholine and the inhibitor of this invention (10 μM each) during the pre-incubation state offers partial protection against inactivation, showing that the inactivation is site-directed, since the substrate binds to the active site on the enzyme (acetylcholinesterase) leaving fewer sites available for inhibitor binding.

In general, the acetylcholinesterase activity in an animal may be reduced and the acetylcholine level elevated by administering to that animal an effective amount of an acetylcholinesterase inhibitor as described herein.

Specifically, the compounds taught by the instant invention are expected to be of utility in the treatment of myasthenia gravis, neurological and ophthalmological disorders, in miotic induction and in the reversal of drug-induced extrapyramidal symptoms which accompany psychiatric drug therapy. In addition, these inhibitors may be used in veterinary medicine for miotic action and for alleviation of colic in horses, as well as, for parallel diseases to those observed in humans, for which human efficacy is known. An effective amount of inhibitor to treat the above abnormalities may be determined on a case by case basis, by those skilled in the art associated with the particular use.

We claim:

1. A chemical compound having the formula:

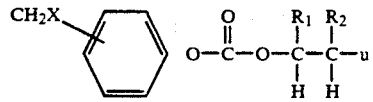

where X=halide or a secondary or tertiary amine; u is

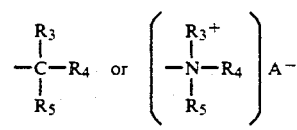

R$_1$, R$_2$, R$_3$, R$_4$ and R$_5$=any one or more members of the group consisting of hydrogen and alkyl groups of up to 5 carbon atoms and A=one more members of the group consisting of iodide, bromide, chloride, acetate and alkylsulfate; said compound having acetylcholinesterase inhibitory activity.

2. A chemical compound, as recited in claim 1, where X=halide.

3. A compound, as recited in claim 1, having the formula:

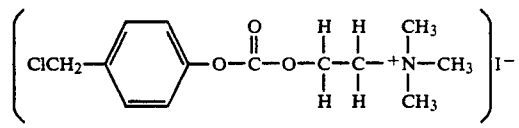

4. A compound, as recited in claim 1, having the formula:

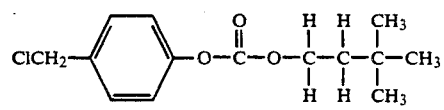

5. A chemical compound, as recited in claim 2, wherein X is iodide.

6. A chemical compound, as recited in claim 5, wherein the halo-alkyl substituent group occupies the paraposition relative to the choline carbonate substituent group.

7. In a method for controlling an insect population of the type wherein an acetylcholinesterase inhibitor is administered to said insects or larva thereof in an insecticidally-effective amount, the improvement comprising employing a compound of claim 1 as the acetylcholinesterase inhibitor.

8. In a method for controlling an insect population of the type wherein an acetylcholinesterase inhibitor is administered to said insects or larva thereof in an insecticidally-effective amount, the improvement comprising employing a compound of claim 2 as the acetylcholinesterase inhibitor.

9. In a method for controlling an insect population of the type wherein an acetylcholinesterase inhibitor is administered to said insects or larva thereof in an insecticidally-effective amount, the improvement comprising employing a compound of claim 3 as the acetylcholinesterase inhibitor.

10. In a method for controlling an insect population of the type wherein an acetylcholinesterase inhibitor is administered to said insects or larva thereof in an insecticidally-effective amount, the improvement comprising employing a compound of claim 4 as the acetylcholinesterase inhibitor.

11. In a method for controlling an insect population of the type wherein an acetylcholinesterase inhibitor is administered to said insects or larva thereof in an insecticidally-effective amount, the improvement comprising employing a compound of claim 5 as the acetylcholinesterase inhibitor.

12. In a method for controlling an insect population of the type wherein an acetylcholinesterase inhibitor is administered to said insects or larva thereof in an insecticidally-effective amount, the improvement comprising employing a compound of claim 6 as the acetylcholinesterase inhibitor.

13. The method of claim 7, wherein the acetylcholinesterase inhibitor comprises the compound of claim 1 in aqueous solution.

14. The method of claim 7, wherein the acetylcholinesterase inhibitor comprises the compound of claim 2 in aqueous solution.

15. The method of claim 7, wherein the acetylcholinesterase inhibitor comprises the compound of claim 3 in aqueous solution.

16. The method of claim 7, wherein the acetylcholinesterase inhibitor comprises the compound of claim 4 in aqueous solution.

17. The method of claim 13, wherein the inhibitor is administered to the insects or larva thereof by spraying.

18. The method of claim 14, wherein the inhibitor is administered to the insects or larva thereof by spraying.

19. The method of claim 15, wherein the inhibitor is administered to the insects or larva thereof by spraying.

20. The method of claim 16, wherein the inhibitor is administered to the insects or larva thereof by spraying.

* * * * *